US012729359B1

(12) United States Patent
Tubbs et al.

(10) Patent No.: US 12,729,359 B1
(45) Date of Patent: Sep. 8, 2026

(54) METHOD OF TESTING GROWTH OF LIVING ORGANISMS IN SPACE

(71) Applicant: Government of the United States, as represented by the Secretary of the Air Force, Wright-Patterson AFB, OH (US)

(72) Inventors: Travis Tubbs, USAF Academy, CO (US); Morgan Vance, Colorado Springs, CO (US)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 482 days.

(21) Appl. No.: 18/475,573

(22) Filed: Sep. 27, 2023

(51) Int. Cl.

| | |
|---|---|
| ***B64G 1/22*** | (2006.01) |
| ***A01G 7/04*** | (2006.01) |
| ***A01G 18/69*** | (2018.01) |
| ***A01K 29/00*** | (2006.01) |
| ***C12M 1/00*** | (2006.01) |
| ***C12M 3/00*** | (2006.01) |
| ***C12N 13/00*** | (2006.01) |

(52) U.S. Cl.
CPC ............ *C12M 23/52* (2013.01); *C12M 23/02* (2013.01); *C12M 23/22* (2013.01); *C12M 23/38* (2013.01); *C12M 23/46* (2013.01); *C12N 13/00* (2013.01)

(58) Field of Classification Search
CPC ...... C12M 23/52; C12M 23/22; C12M 23/38; C12M 23/46; C12N 13/00; A01G 7/045; A01G 18/69; A01K 29/005
See application file for complete search history.

(56) References Cited

U.S. PATENT DOCUMENTS

| | | | |
|---|---|---|---|
| 3,749,332 | A | 7/1973 | Gray |
| 3,847,200 | A | 11/1974 | Kopp |
| 4,792,108 | A | 12/1988 | Bull |

(Continued)

FOREIGN PATENT DOCUMENTS

| | | | | | |
|---|---|---|---|---|---|
| CN | 114391399 | B | * | 1/2023 | ............. A01G 7/045 |
| CN | 116034776 | A | * | 5/2023 | ............... A01G 9/16 |
| WO | 2008144899 | A1 | | 12/2008 | |

OTHER PUBLICATIONS

Present inventor, Tubbs. Cadets Create Plant Experiment to go to Space. US Air force Academy. Believed to be uploaded to the Internet Sep. 30, 2022. https://www.usafa.edu/cadets-create-plant-experiment-to-go-to-space/#:~:text=Ultimately%20the%20aim%20is%20to,in%20the%20microgravity%20of%20space.

(Continued)

*Primary Examiner* — Lydia Edwards
(74) *Attorney, Agent, or Firm* — AFMCLO/JAZ; Larry L. Huston

(57) ABSTRACT

A method of testing living organisms in space. On earth a chamber is loaded with at least one cuvette having a living organism for experimentation. The chamber and cuvette are placed aboard a transport vehicle for transport to and return from space. The cuvette is maintained at atmospheric pressure throughout transport and during the time in space. The cuvette remains at atmospheric pressure, even throughout extra vehicular activities during transport. This method provides for the transport vehicle to be subjected to the vacuum of space without damage to the living organism or disrupting any experiment involving the living organism.

8 Claims, 13 Drawing Sheets

(56) References Cited

U.S. PATENT DOCUMENTS

| | | | |
|---|---|---|---|
| 5,475,610 | A | 12/1995 | Atwood |
| 7,387,891 | B2 | 6/2008 | Boege |
| 10,813,295 | B2 | 10/2020 | Alexander |
| 2008/0176209 | A1 | 7/2008 | Muller |
| 2009/0000189 | A1 | 1/2009 | Black |
| 2013/0305606 | A1 | 11/2013 | Lonsdale |
| 2013/0329417 | A1 | 12/2013 | Goeschl |
| 2015/0027052 | A1 | 1/2015 | Janssen |
| 2017/0196172 | A1 | 7/2017 | Ejiri |
| 2019/0374665 | A1 | 12/2019 | Jo |
| 2020/0386734 | A1 | 12/2020 | Irritier |

OTHER PUBLICATIONS

Editor Heiney. Growing plants in Space. NASA, Exploration Research and Technology. https://www.nasa.gov/content/growing-plants-in-space.

* cited by examiner 15H
33R
11
10
19

13
56
55
55
56
55
56
56
55
56
56S
55
56R
30
30

15H
15
40
44
17
11
12
19
41
44
10
13

METHOD OF TESTING GROWTH OF LIVING ORGANISMS IN SPACE

STATEMENT OF GOVERNMENT INTEREST

The invention described and claimed herein may be manufactured, licensed and used by and for the Government of the United States of America for all government purposes without the payment of any royalty.

FIELD OF THE INVENTION

The present invention is related to a method of growing living organisms in space and more particularly to a method of growing of living organisms while in a transport vehicle which can be subjected to the vacuum of space.

BACKGROUND OF THE INVENTION

On Jun. 22, 1973 Skylab 2 Commander Charles Conrad, Pilot Paul Weitz and Science Pilot Joseph Kerwin completed a 28-day space mission. On Feb. 8, 1974 Skylab 4 Commander Gerald Carr, Pilot William Pogue and Science Pilot Edward Gibson completed an 84 day mission of space science experiments. During this mission they completed four Extravehicular Activities [EVA]. For more than 50 years there has been a need to accommodate EVAs in space.

On Jan. 25, 1984 at his State of the Union Address President Regan directed NASA to build an international space station [ISS]. On Nov. 20, 1998 Russia launched the first segment of the ISS, the Zarya module, aboard a rocket launched from Kazakhstan. On Dec. 4, 1998 the US launched its Unity Node 1 module of the ISS by space Shuttle Endeavour. On Nov. 2, 2000 NASA Expedition 1 Commander Bill Shepherd and Cosmonaut Flight Engineer and Soyuz Commander Yuri Gidzenko and Flight Engineer Sergei Krikalev became the first crew to reside on the ISS, remaining for a period of four months. On Feb. 7, 2008 the European Lab joined the ISS, followed by the Japanese Lab on Mar. 11, 2008. Participation in the ISS now includes the United States, Russia, Japan, Canada, Belgium, Denmark, France, Germany, Italy, The Netherlands, Norway, Spain, Sweden, Switzerland, and The United Kingdom. The ISS has been continuously occupied by men and women from various continents for more than 20 years.

For more than 50 years, a common denominator across all of the people from all of the continents who have occupied Skylab, the ISS and the Russian space stations is need for sustenance and nutrition. And more recently the need has been recognized for fresh and more tasty foods aboard long space missions. During a two to three year mission to Mars, the vitamins and quality of packaged food would degrade over time. Supplementation with fresh, edible crops will provide necessary nutrients while also enhancing dietary variety. Anecdotal evidence also supports the potential for psychological benefits for astronauts, rooted in the enjoyment of eating and caring for the plants.

NASA has responded to this need for several years with various attempts to grow plants in space. For example, Apr. 18, 2014 NASA launched the Vegetable Production System [Veggie], to attempt to grow fresh food for astronauts in order to supplement their diet and use as a tool to support relaxation and recreation. On May 7, 2014 Astronauts Rick Mastracchio and Steve Swanson installed Veggie in the Columbus Laboratory Module. Veggie drains about 70 watts for lights, fans and control electronics. Veggie uses passive wicking and relies upon the cabin environment on the ISS for temperature control and a source of carbon dioxide. The first crop was lettuce which grew for 33 days, followed by several other crop experiments.

Further attempts in the art include the Advanced Plant Habitat (Plant Habitat) aboard the ISS, which provides an environmentally controlled chamber to support plant research on the ISS for at least one year of continuous operation with only maintenance of consumables. The Plant Habitat integrates microgravity plant growth technologies and provides a window for the crew to view the progress of the plants while maintaining the single level of containment. The Plant Habitat has 180 calibrated sensors so that the system can function autonomously using a pre-programmed experimental design. This design provides a suitable growth environment (e.g., temperature, relative humidity, carbon dioxide level, light intensity and spectral quality) for plant experiments of up to 135 days duration.

But all of these experiments and attempts over the last 50 years fail to account for the transport vehicle which transports the experiments to and from the Skylab, ISS or other long term space habitat. As used herein the transport vehicle refers to the spacecraft which originates from earth, the ISS or other manmade space habitat for transportation of supplies, personnel and experiments therebetween. The transport vehicles may be provided by NASA, SpaceX, Blue Origin, the Space Force, etc. The transport vehicle may be discarded in whole or in part after a single use or may be restored and reused.

But the transport vehicle may provide more functionality than merely transporting supplies, experiments and personnel between the earth and ISS, etc. For example, it may be desirable—or even necessary—to perform an EVA during transport and particularly during space travel. The EVA may be necessary for inspection, to perform maintenance on the transport vehicle, the ISS or satellites, to perform experiments, to gather data, etc.

But the EVA subjects the transport vehicle to the vacuum of space when the astronauts open the hatch for egress and ingress. Any living organism in the transport vehicle would boil when subjected to the vacuum of space and the value of the intended experiment would be lost.

Accordingly, this invention overcomes the problem of transporting experimental living organisms into space on transport vehicles which are subject to EVA.

SUMMARY OF THE INVENTION

In one embodiment the invention comprises a method of testing living organisms in space. The method comprises the steps of: on earth providing a chamber for removably receiving a plurality of elongate cuvettes therein, the chamber having a base and an illumination lid remote therefrom, a plurality of receptacles between the base and lid, each receptacle being sized to removably receive at least one respective cuvette therein, each cuvette having a proximal end and a translucent distal end longitudinally opposed thereto and juxtaposed with the illumination lid; on earth disposing at least one living organism in each cuvette of a first plurality of cuvettes, to be in contacting with a growth medium disposed therein; on earth disposing the first plurality of cuvettes with the living organisms therein in the receptacles of the chamber to thereby impart artificial light from the illumination lid to the living organisms while in the first plurality of cuvettes; transporting the chamber to the international space station for removal from earth gravity for an extended period; and returning the chamber with the first plurality of cuvettes having the living organisms therein to earth for analysis of the living organisms.

Figure 1A:
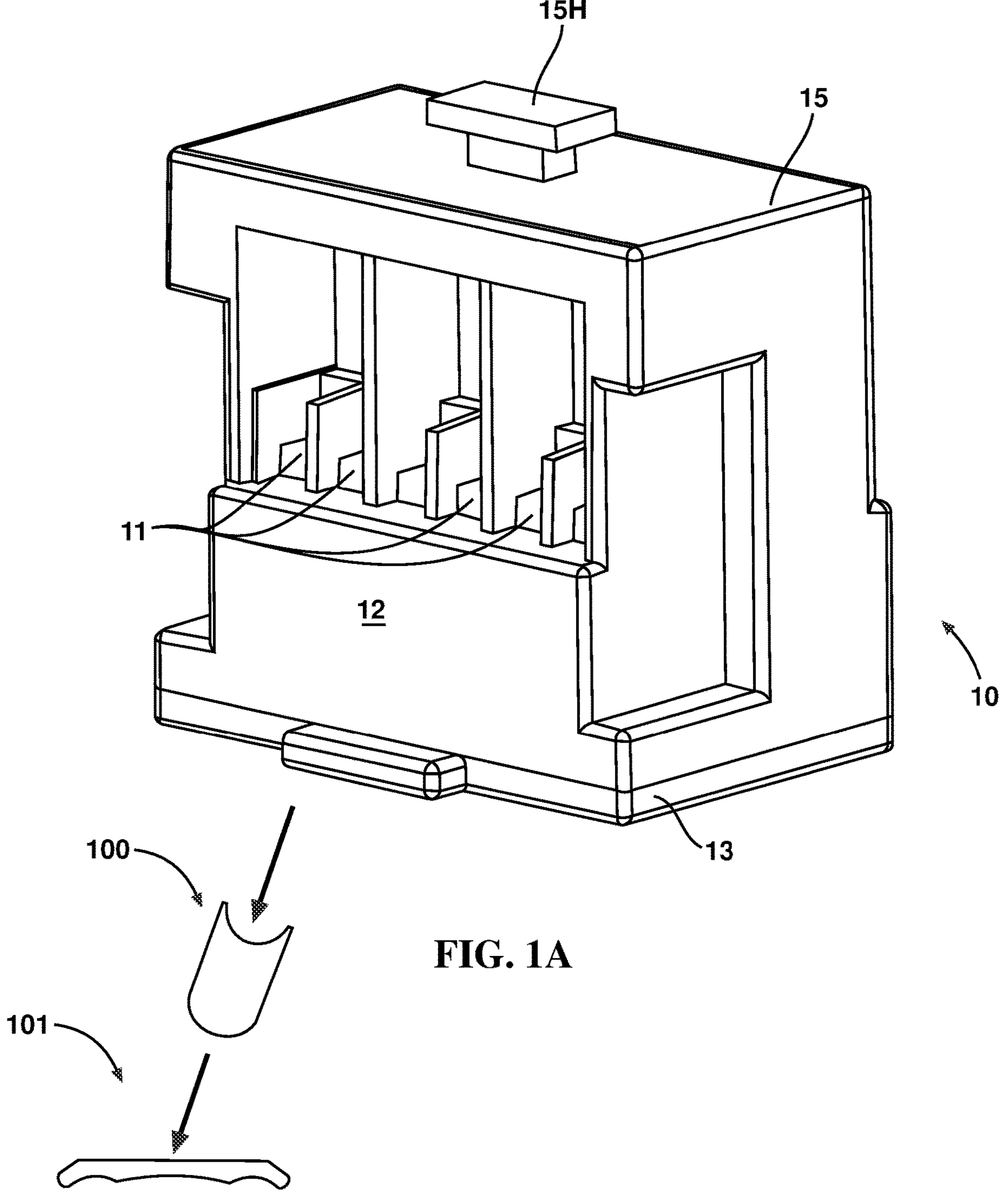
FIG. 1A is a scale perspective view of a chamber according to the present invention, with a schematic transport vehicle and schematic international space station.
Figure 1B:
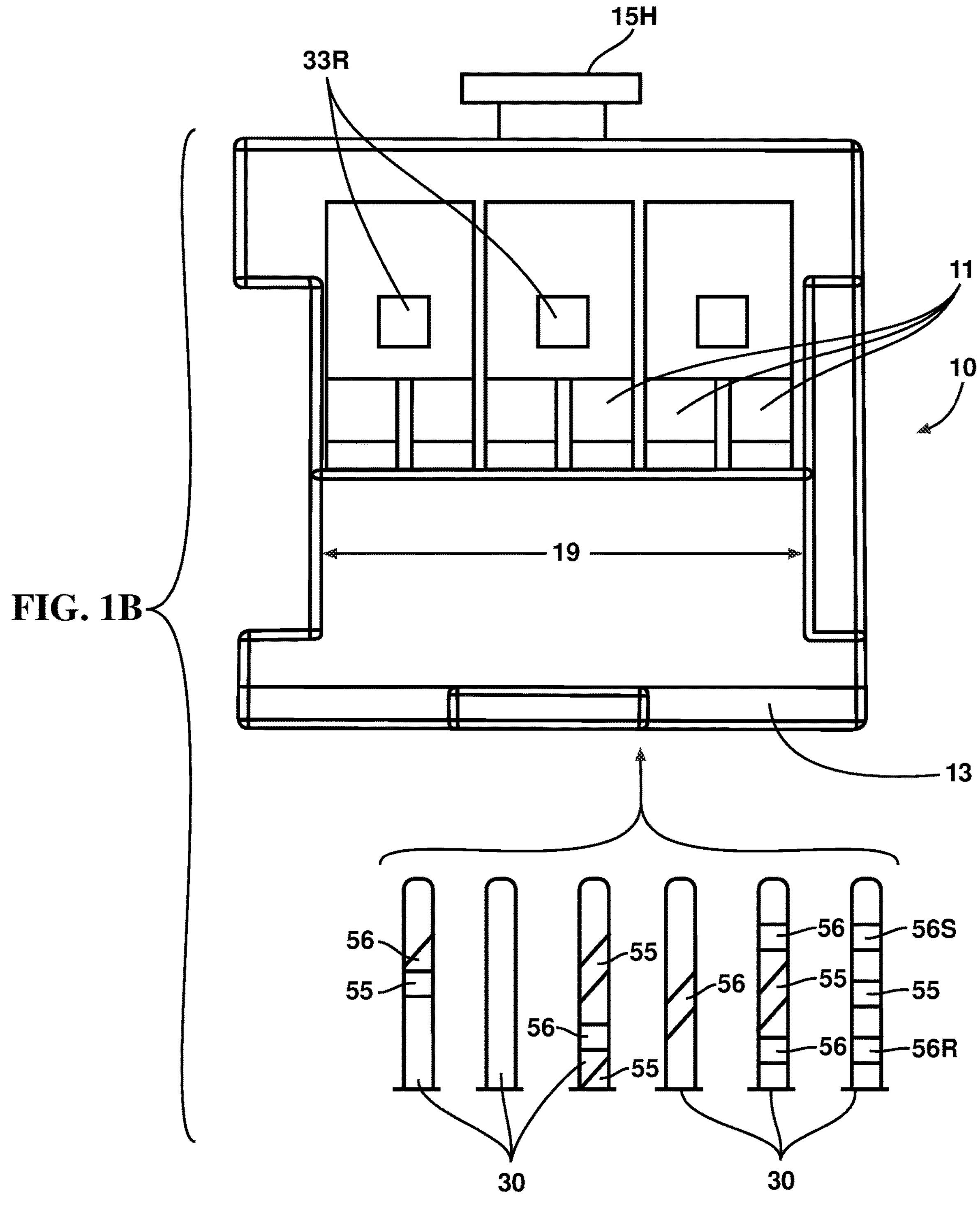
FIG. 1B is a scale front elevational view of the view of the chamber of FIG. 1A, showing squares above the half walls [what are the squares?] and six schematic cuvettes.
Figure 1C:
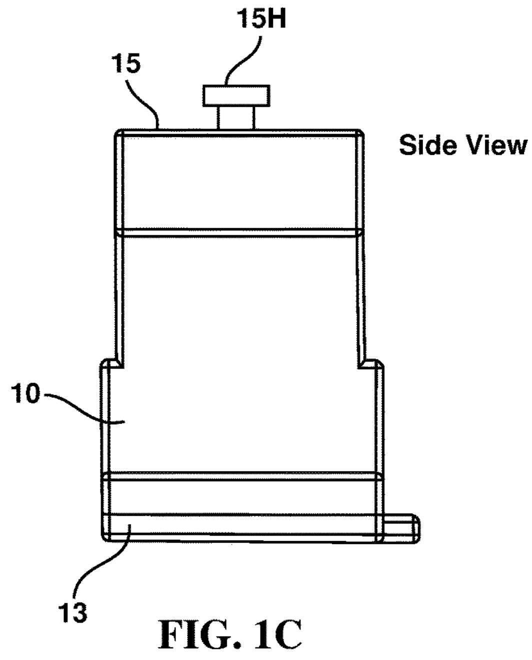
FIG. 1C is a scale left side elevational view of the chamber of FIG. 1A.
Figure 1D:
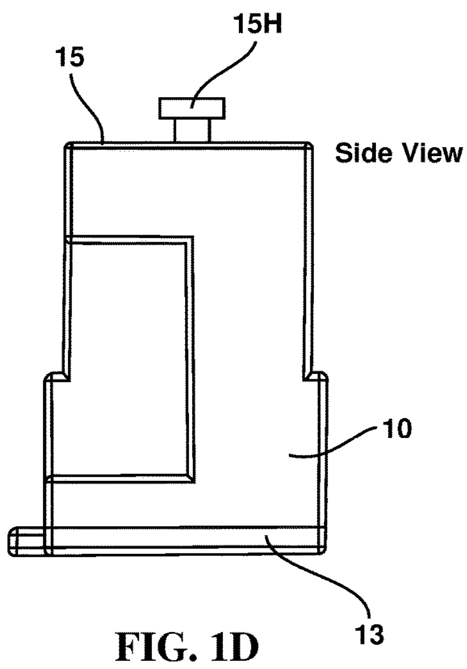
FIG. 1D is a scale right side elevational view of the chamber of FIG. 1A.
Figure 1E:
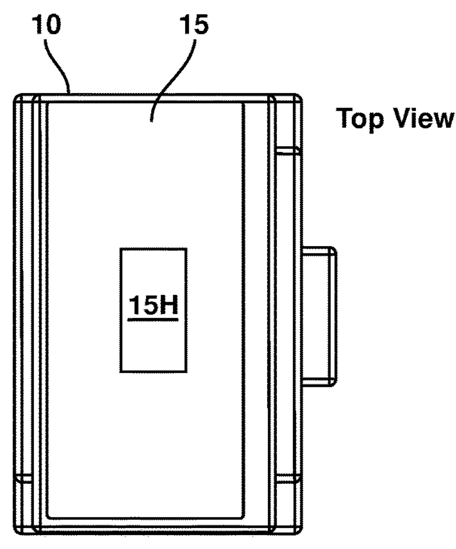
FIG. 1E is a scale top plan view of the chamber of FIGS. 1A and 1B, shown partly in cutaway.
Figure 1F:
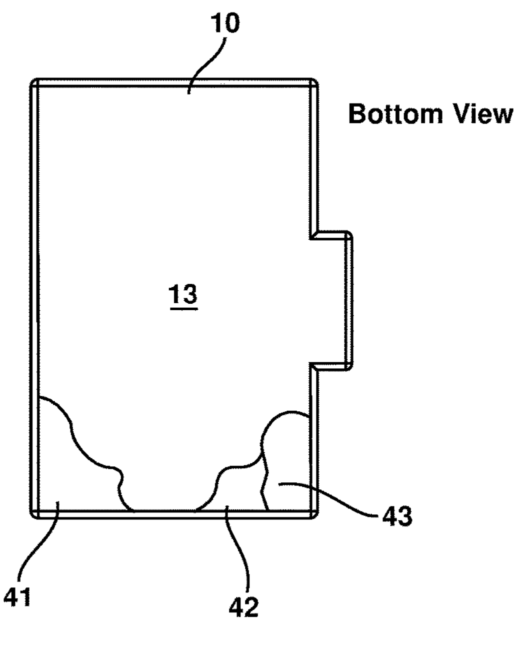
FIG. 1F is a scale bottom plan view of the chamber of FIG. 1A, shown partly in cutaway to reveal a schematic battery, controller and data logger.

The battery, controller and data logger are shown in schematic throughout all drawings where illustrated.

DETAILED DESCRIPTION OF THE INVENTION

Referring to FIGS. 1A-1F, the invention comprises a chamber 10 for selectively growing living organisms 56 in space. The chamber 10 comprises receptacles 11 for removably holding complementary cuvettes 30 therein, a lid 15 for selectively covering the receptacles 11, a base 13 for supporting the receptacles 11 and other components of the chamber 10 and a chassis 12 therebetween.

Preferably the chamber 10, when fully loaded with cuvettes 30, has a volume of preferably less than 1500 cc, to conserve valuable space on both the transport vehicle 101 and the ISS 101. More preferably the fully loaded chamber 10 has a volume less than 1000 cc [one liter] to comply with constraints imposed by SpaceX for its transport vehicles 101.

Examining the receptacles 11 in more detail, the receptacles 11 may be equal in size and or shape as shown or may be unequally sized, according to the desired cuvette(s) to be inserted into and removed therefrom. While receptacles 11 having only a single cuvette 30 therein is shown, the invention is not so limited. Plural cuvettes 30 may be disposed in a single complementary receptacle, receptacles 11 may be left empty as needed for the particular experiments, etc.

By complementary it is meant that the cuvettes 30 and receptacles 11 are sized, shaped and available so that cuvettes 30 can be inserted into and removed from the receptacles 11 without undue time or manipulation and preferably without tools. Preferably the cuvettes 30 are retained in fixed relationship within the respective, complementary receptacles 11 by a friction fit, although the invention is not so limited. The use latches, hook and loop fasteners 13, adhesive and clips are contemplated for retaining the cuvettes 30 in the receptacles 11. It is only necessary to retain the cuvettes 30 as needed within the chamber 10 for control of experimental conditions of living organism 56 within the cuvettes 30.

The receptacles 11 may be open in the front for direct access to and viewing of the cuvettes 30 on earth, during transport to and abord the ISS 101. The receptacles 11 may have a solid back for support and to provide a space for other components of the chamber 10. The sides of the receptacles 11 may be solid, intercepting the entire corresponding wall of a cuvette, may be perforate and/or may extend less than the full length or depth of a receptacle. The sides of the receptacles 11 define and separate adjacent receptacles 11.

The receptacles 11 may be disposed in rows 19 within the chamber 10, and particularly the chassis 12 thereof. The rows 19 may have unequal or preferably equally numbers of receptacles 11 and be of unequal or preferably equal length. The receptacles 11 may be outwardly and oppositely spaced in the rows 19, so that cuvettes 30 may be conveniently accessed. The rows 19 may be in any desired configuration, but are preferably straight to preserve consistent test conditions, parallel and coterminous to conserve volume and meet volume requirements. The receptacles 11 may be equal or unequal in size, as desired for the complementary cuvettes 30 needed for the particular experiment under consideration. The rows 19 of receptacles 11 may define a chassis 12 direction parallel to the longest direction of the chassis 12, and generally parallel to the width direction thereof.

Examining the invention in more detail, the base 13 of the chamber 10 may be solid or is preferably hollow to conserve weight. A hollow base 13 may contain one or more batteries 41, a data logger 43, a controller 42 and other components therein. The base 13 may be removably attached to the chassis 12 with magnets 51, clips a friction fit or other known means. Preferably the base 13 does not require a screwdriver or other tools to be removed from or attached to the chassis 12.

If desired, the base 13, or any other portion of the chamber 10, may be provided with hook and loop fasteners 13 for removable attachment to complementary hook and loop 13 material disposed in fixed position on the ISS 101 or transport vehicle 101. Alternatively, a tether may be used to keep the chamber 10 in place.

The illuminable lid 15 is likewise removably attachable to the chassis 12 with magnets 51, clips a friction fit or other known means. And likewise the lid 15 may be solid or is preferably hollow to conserve weight. A hollow lid 15 may likewise contain one or more batteries 41, a data logger 43, a controller 42 and other components therein. The lid 15 has an inner surface facing towards the chassis 12 when the lid 15 is in place and an outer surface opposed thereto. The lid 15 may have a handle 15H, as shown, for ergonomics or may be provided without a handle 15H to conserve volume.

Figure 2:
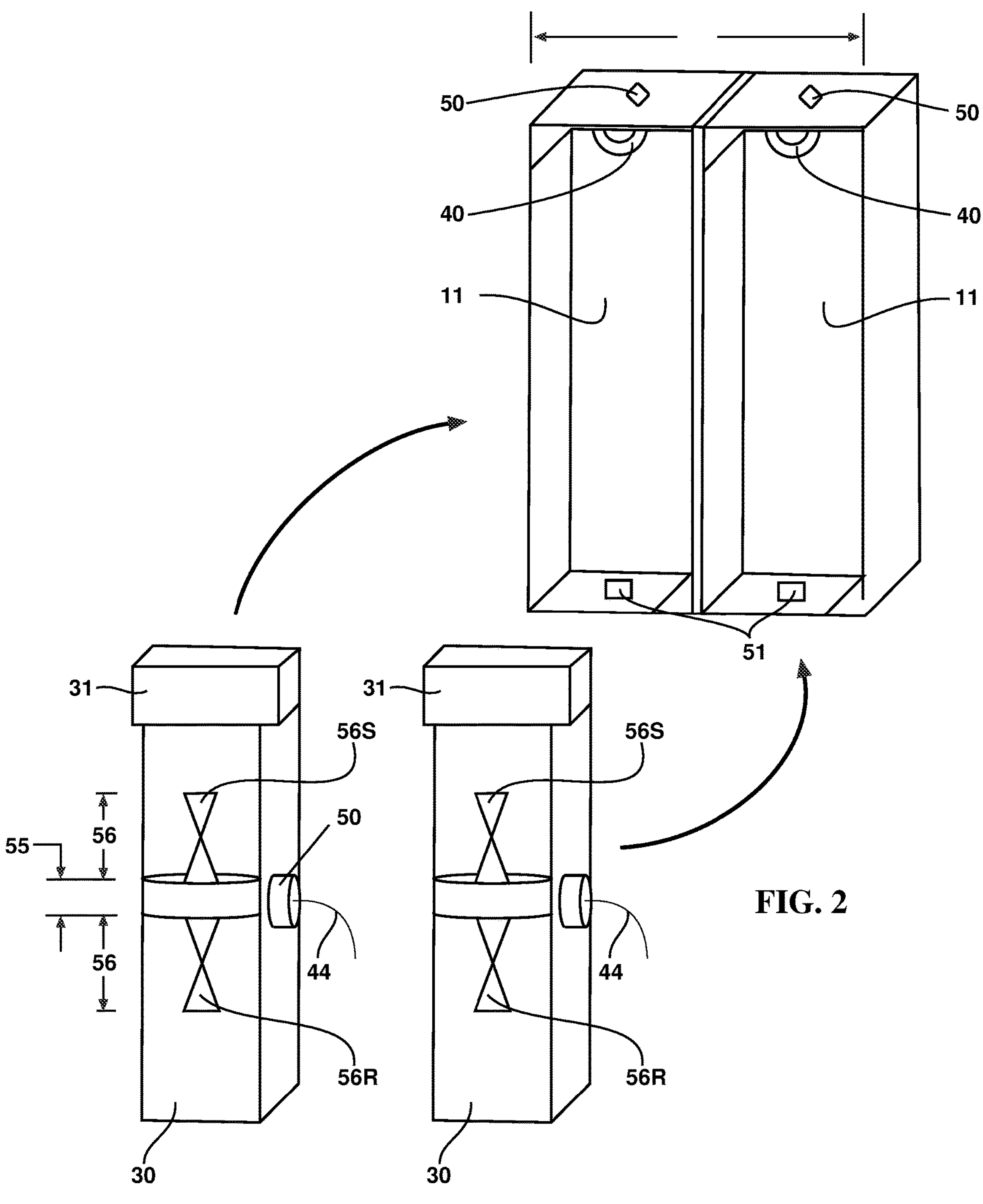
FIG. 2 is a schematic perspective view of two receptacles and two respective cuvettes for installation in the receptacles in the direction of the arrows.

Referring to FIG. 2 one or more cuvettes 30 are insertable into and removable from the receptacle. Within the cuvettes 30 may be one or more living organisms 56 and optionally one or more growth media 55 therefor. A single cuvette 30 may have plural living organisms 56 which are identical or different and plural growth media 55 which are identical or different.

One or more receptacles 11 may have a magnet 51 juxtaposed therewith. The magnet 51 may be used to provide a magnetic field to test the influence of the magnetic field on one or more living organisms 56 in the cuvettes 30. Optionally the chassis 12 may have a pocket to receive the magnet 51 while maintaining a flush surface to conserve space.

The cuvettes 30 are preferably elongate, to provide linear growth space for living organism 56 therein. The major axis of the cuvettes 30 may be generally perpendicular to the chassis 12 direction of the rows 19 of receptacles 11. The cuvettes 30 may be generally parallelpidally shaped for convenience and improved packing density when installed in the receptacles 11.

The cuvettes 30 provide the important function of protecting living organism 56 therein when the chamber 10 is subjected to the vacuum of space. This arrangement provides the significant benefit that during transport to and from the ISS 101 the astronauts of the transport vehicle 101 may engage in EVA without damage to the living organism 56. The inside of the cuvettes 30 remain at atmospheric pressure during the EVA when the rest of the cabin is subject to the vacuum of space.

The cuvettes 30 have a removable cap 31 to allow for insertion and removal of growth medium 55 and living organism 56 for testing and subsequent analysis. The removable cap 31 may be disposed anywhere on the cuvette. For convenience, the removable cap 31 may be disposed at one end of the cuvette. Optionally the cuvette 30 may have a removable cap 31 at both ends thereof. This arrangement provides for enhanced evacuation and cleaning of the cuvette, but increases the risk of leakage when subjected to vacuum. The removable cap 31 may be joined to the walls of the cuvette 30 by a friction fit and/or space approved adhesive.

The cap 31 is preferably translucent, to allow transmission of light 40 therethrough so that the light 40 can reach the growth medium 55 and more particularly the living organism 56 in the cuvette. As used herein, translucence includes transparency, or any configuration which allows the cap 31 to transmit light 40 therethrough and maintain atmospheric pressure in the cuvette 30 in the presence of the vacuum of space. The cap 31 may be actinically translucent, according to the particular wavelengths of light 40 for the experiments under consideration.

Figure 3:
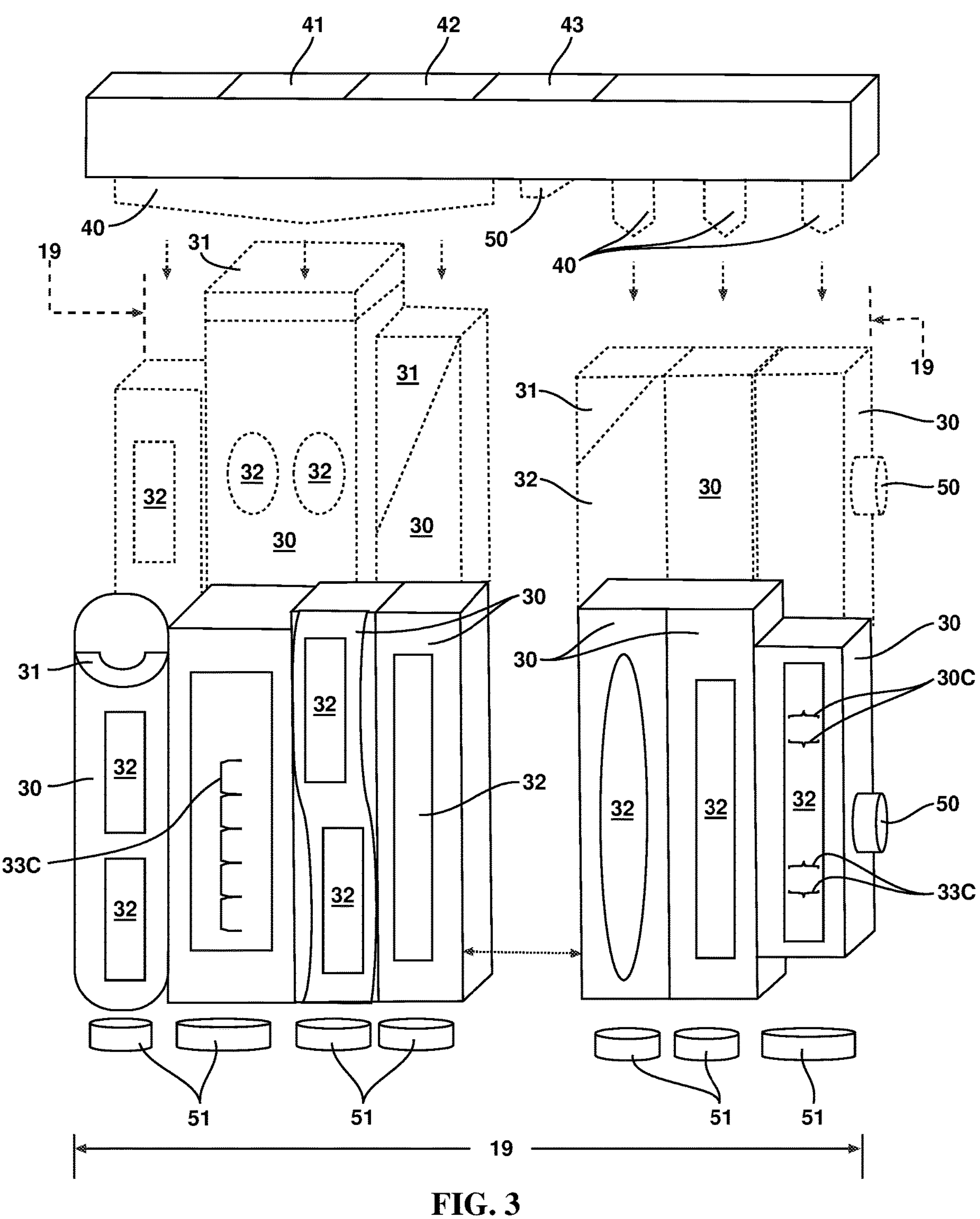
FIG. 3 is a scale perspective view of two indeterminate length rows of variable size scale cuvettes, with schematic sensors and a schematic lid having schematic lights, battery, controller and data logger, with the front row shown in solid and the back row shown in dashed.

Referring to FIG. 3, if desired, the chamber 10 may have plural opposed and corresponding rows 19 of receptacles 11. An experiment may call for a first row 19 of receptacles 11, and more particularly living organisms 56 disposed in cuvettes 30 received in the first row, to be exposed to a magnetic field. And the same experiment may call for a second row 19 of receptacles 11, and more particularly living organisms 56 disposed in cuvettes 30 received in the second row, not to be exposed to that magnetic field.

The illuminable lid 15 is provided with one or more lights 40, such as but not limited to LED lights 40, to provide artificial light 40 to living organism 56 within the cuvettes 30. Particularly, the lid 15 may have one or more batteries 41 therein or may be wired from one or more batteries 41 in the chassis 12 and/or the base 13. The lights 40 are disposed to project artificial light 40 towards the direction of the cuvettes 30 and particularly the translucent end cap 31 thereof.

The illuminable lid 15, as defined herein includes one or more lights 40 as suitable for illuminating at least a portion of, and preferably all of the cuvettes 30 in a particular row 19 of receptacles 11 and a power source for such lights 40. The power source may be one or more batteries 41 as needed to power the lights 40, direct energy conversion from ambient light, etc. Particularly, each receptacle 11 may have a respective LED light 40 dedicated thereto.

The lights 40 may be provided with different color spectrums as desired for different chromic effects on the living organism 56. For example, a first color of artificial light 40 may be used for the first time period of an experiment, a second color of artificial light 40 may be used for the second time period of an experiment, the intensity of the artificial light 40 may be increased or decreased for a third time period of the experiment, etc. The characteristics of the artificial light 40 may be manually adjusted in response to observations of the living organism 56, may be automatically adjusted by a controller 42 or combinations thereof.

The cuvettes 30 have a transparent window 32 in at least one wall. The window 32 preferably faces outwardly when the cuvette 30 is placed in the complementary receptacle, to allow for unobstructed viewing by the experimenter. In a preferred embodiment, the cuvette 30 may have four transparent walls, to provide for unobstructed viewing throughout and in any direction. The transparent window 32 and/or transparent wall of the cuvette 30 may be provided with indicia 33C to assist in measuring growth, movement and other progress of the living organism 56 during the course of the experiment. This arrangement provides the benefit that different indicia 33C may be used for different experiments. Such indicia 33C may be tailored as desired simply by changing the cuvette 11 to a cuvette 11 having a different indicium 33C.

Figure 4A:
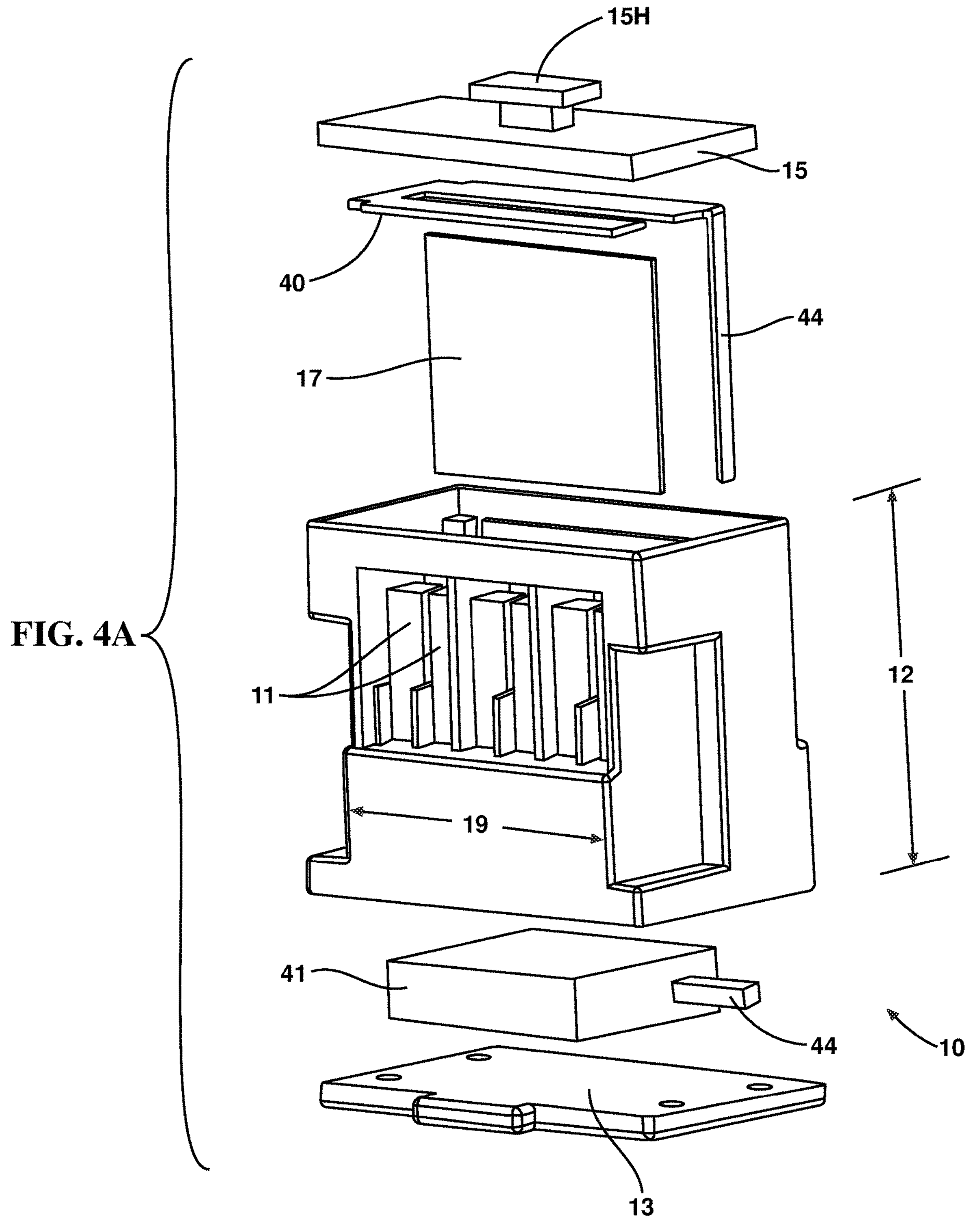
FIG. 4A is a scale exploded perspective view of the chamber of FIG. 1A.

Referring to FIG. 4A, a lead 44 may connect the lid 15 to the base 13 for electrical communication therebetween. The lead 44 may provide for battery 41 power transmission from the base 13 to the lid 15, data transfer from the lid 15 to the base 13, etc.

A partition 17 may be interposed between the first row 19 of receptacles 11 and second row 19 of receptacles 11. Such a chamber 10 may have a slot 18 intermediate the first row 19 of receptacles 11 and second row 19 of receptacles 11 for removably receiving the partition 17. The slot 18, and the partition 17 inserted therein, may be generally planar and generally parallel to the planes of the first and second rows 19 of receptacles 11.

The partition 17 may be made of any material which absorbs the magnetic field. Suitable materials include those which conform to ASTM A753 Alloy Type 4 and MIL-N-14411 Composition 1, and more preferably conform to ASTM A753 Alloy Type 2 and MIL-N-14411 Composition 3. Alloy 49 and MuMetal are believed to be suitable.

Figure 4B:
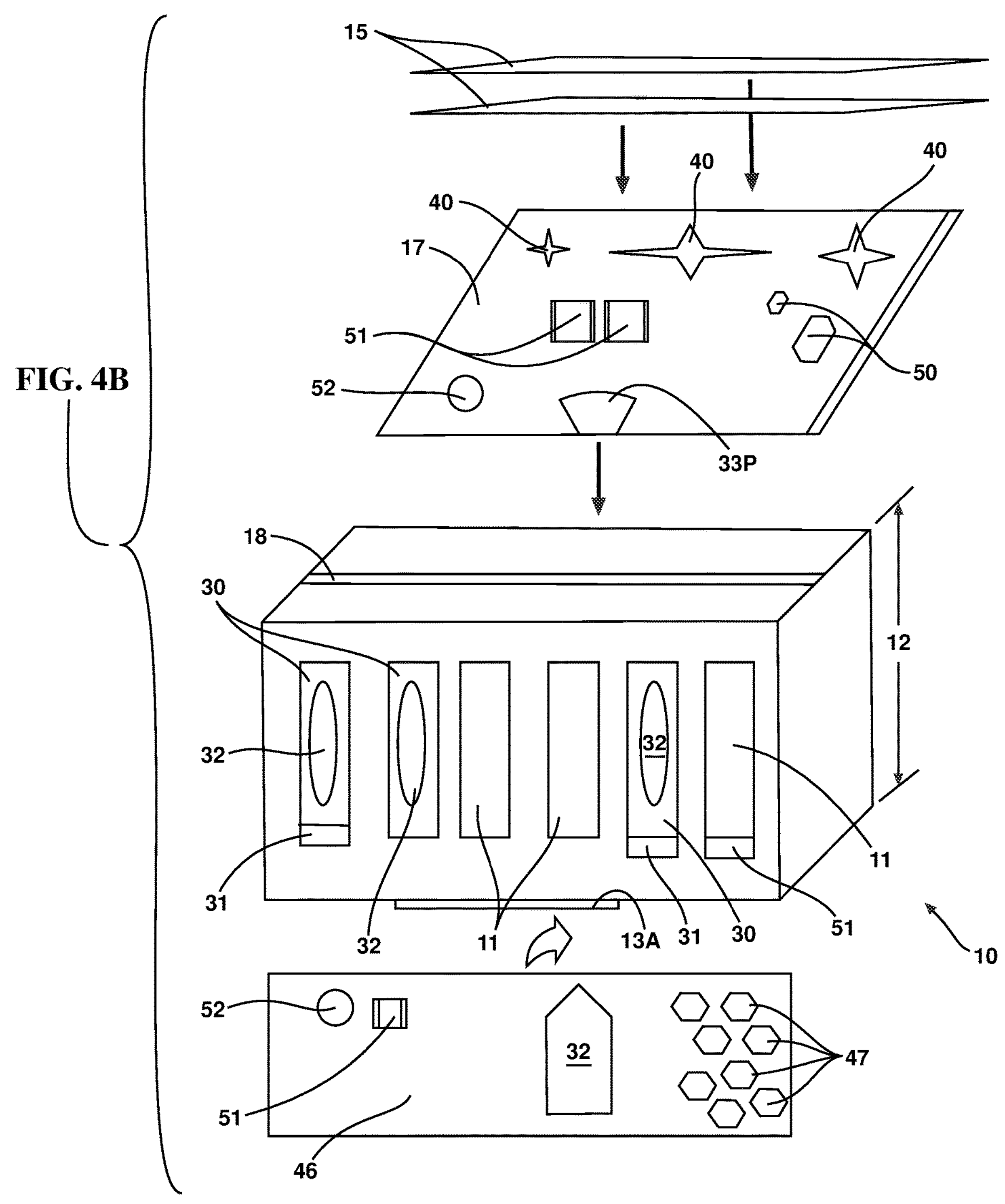
FIG. 4B is a schematic exploded fragmentary perspective view of an alternative chamber having an active partition, dual lids and a side panel.

Referring to FIG. 4B, the partition 17 may be active and particularly may be illuminated. In an illustrative and non-limiting embodiment, the partition 17 may have a one light 40 or a plurality of lights 40 disposed thereon. The lights 40 may be unequally sized, spaced and colored to provide different amounts, wavelengths and intensities of illumination to respective cuvettes 30 in the chamber 10, with three different lights 40 being shown. The partition 17 lights 40 may be used instead of or in addition to lights 40 projecting downwardly from the lid 15 and/or upwardly from base 13.

Likewise, in an illustrative and nonlimiting embodiment, the partition 17 may have one magnet 51 or a plurality of magnets 51 disposed thereon. The magnets 51 may be unequally sized, spaced and configured to provide different magnetic fields to respective cuvettes 30 in the chamber 10, with two different magnets 51 being shown. The partition 17 magnets 51 may be used instead of or in addition to magnets 51 projecting downwardly from the lid 15 and/or upwardly from base 13. A single magnet 51 and/or a single light 40 disposed on the lid 15, partition 17 and/or base 13 may be dedicated to a particular receptacle 11 or to a plurality of receptacles 11, which receptacles 11 are preferably adjacent.

The partition 17 may have one or more sensors 50 thereon. Exemplary and nonlimiting sensors 50 for the chamber 10 and cuvettes 30 described herein include thermometers, magnetometers, Geiger-Müller counters, lux meters, etc. The partition 17 may be provided with a camera 52 for close up photography of experiments.

The partition 17 may be sided, i.e. have different components on the opposed faces thereof. The partition 17 may have indicia 33P designating which face is oriented towards the front of the chamber 10, instructions for experiments, etc. This arrangement provides the benefit that the partition 17 may have different indicia 33P on each side thereof, to accommodate different experiments in opposed rows 19. Or the partition 17 may be entirely swapped out to for alternative indicia 3P, or none at all, without disturbing a permanent indicium 33R in the chamber 10.

While a partition 17 parallel to the row 19 direction, i.e. the width direction, of the chamber 10 is shown, one of skill will recognize the invention is not so limited. The chamber 10 may have a partition 17 which perpendicularly bisects the rows 19 of receptacles 11, or otherwise cuts across one or more rows 19 of the receptacles 11. Or the chamber 10 may have plural partitions 17, with partitions 17 both parallel to and perpendicular to the rows 19 of receptacles 11.

The top of the chamber 10, with or without the partition 17, may be covered by one or more lids 15 to protect the cuvettes 30, retain the cuvettes 30 with the respective receptacles 11, provide illumination to the cuvettes 30, etc. If desired, a single lid 15 may cover all of the rows 19 of receptacles 11. Alternatively, as shown, the chamber 10 may have plural lids 15. This arrangement provides the benefit that each row 19 may have one or more dedicated lid(s) 15, tailored to the particular conditions desired for that row 19 or portion thereof. For example, a lid 15 covering a first row, or portion thereof, may have lights 40, magnets 51, heaters, sensors 50, etc. thereon. A lid 15 covering an adjacent row, or portion thereof, may have a different combination of lights 40, magnets 51, heater, sensors 50, etc. thereon. Etc.

The chamber 10 may have side panels 46 to cover the open faces of the receptacles 11, and any cuvettes 30 disposed therein. The side panels 46 may be used to protect the receptacles 11, and cuvettes 30 therein, from ambient conditions such as radiation, light, physical disturbances, thermal differences, etc. The side panels 46 may be transparent or opaque. The side panels 46 may removably attach to the chassis 12 in known fashion by magnets 51, clips, hook and loop fasteners 13, tabs, etc. The side panels 46 may also have any of the aforementioned sensors 50 and/or camera 52.

While a chamber 10 having a single side panel 46 which covers an entire row 19 of receptacles 11 is shown, one of skill will recognize the invention is not so limited. The chamber 10 may have two side panels 46 covering two opposed rows 19 of receptacles 11. The two side panels 46 may be identical or different, as desired. Or a side panel 46 may cover only a portion of the row 19 of receptacles 11, so that other cuvettes 30 may be directly accessed without removing the side panel. The side panel 46 may be solid and opaque for maximum protection. The side panel 46 may be opaque with a transparent window 32 therethough for observation without removal of the panel from the chassis 12. The side panel 46 may be perforate, having perforations 47 to conserve weight or have combinations of any of these embodiments.

Figure 5A:
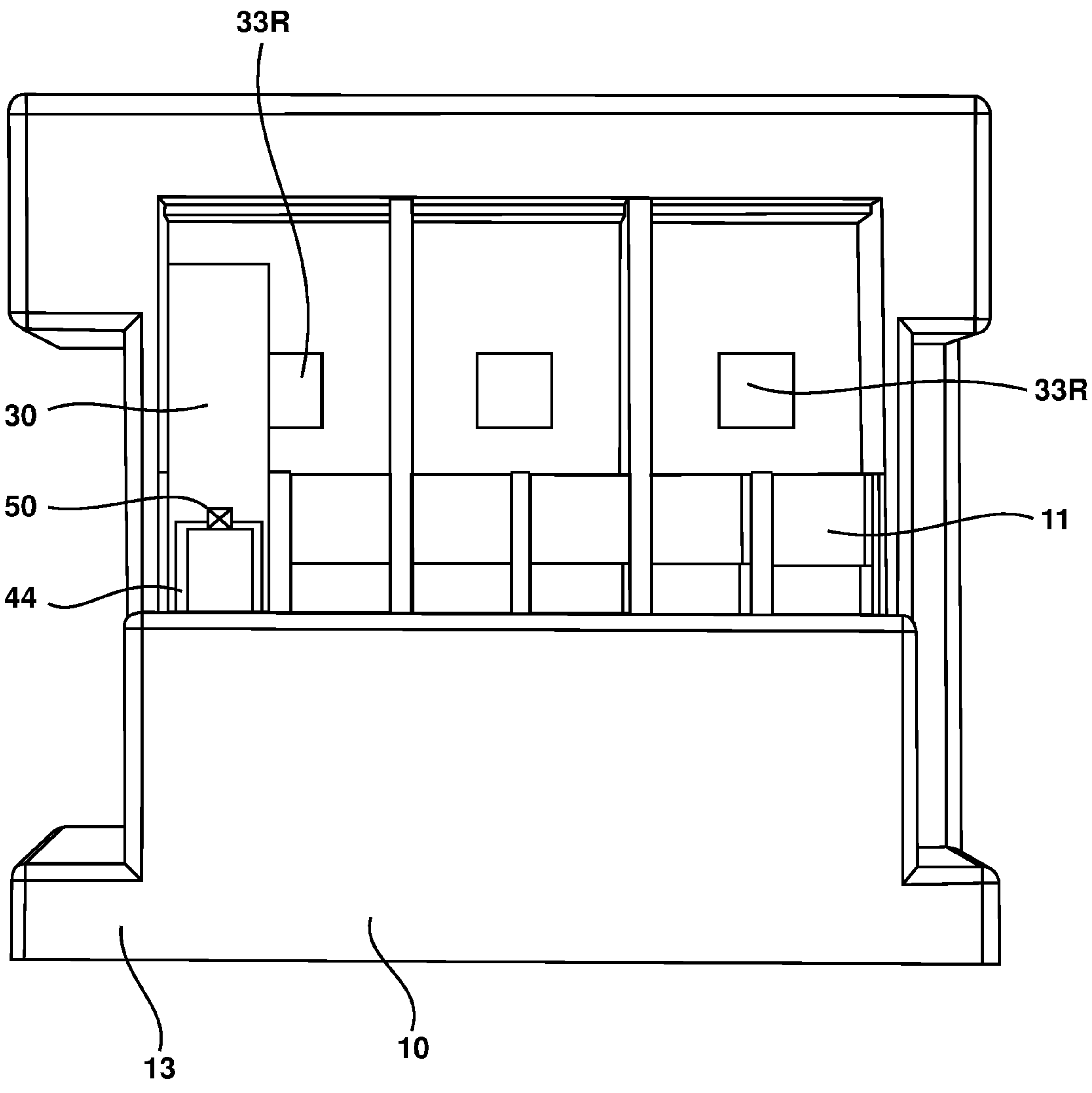
FIG. 5A is a scale front elevational view of a chamber having an alternative embodiment of a cuvette therein.
Figure 5B:
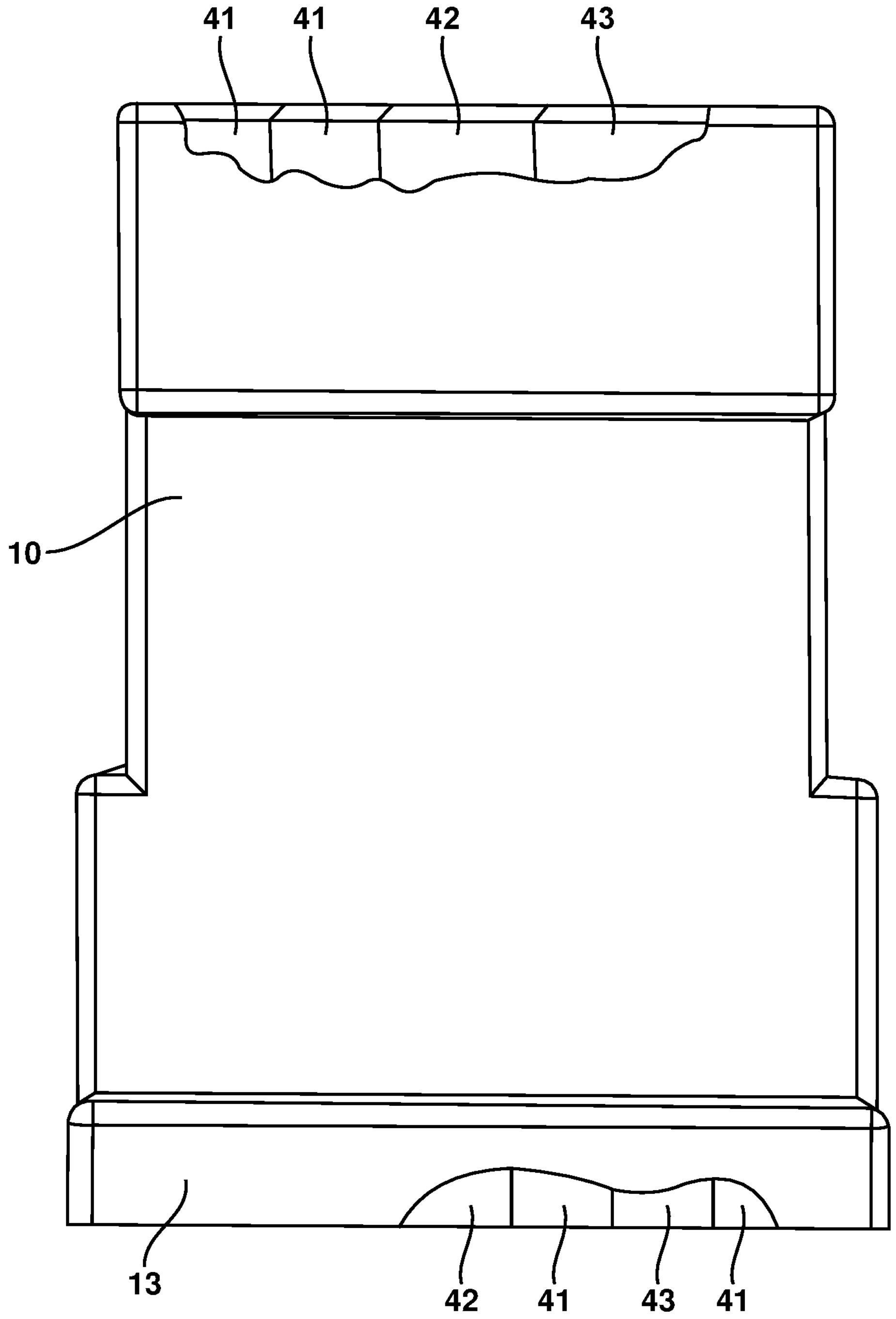
FIG. 5B is a scale rear elevational view of the chamber of FIG. 5A, shown partially in cutaway to reveal a battery, controller and data logger in each of the lid and base.
Figure 5C:
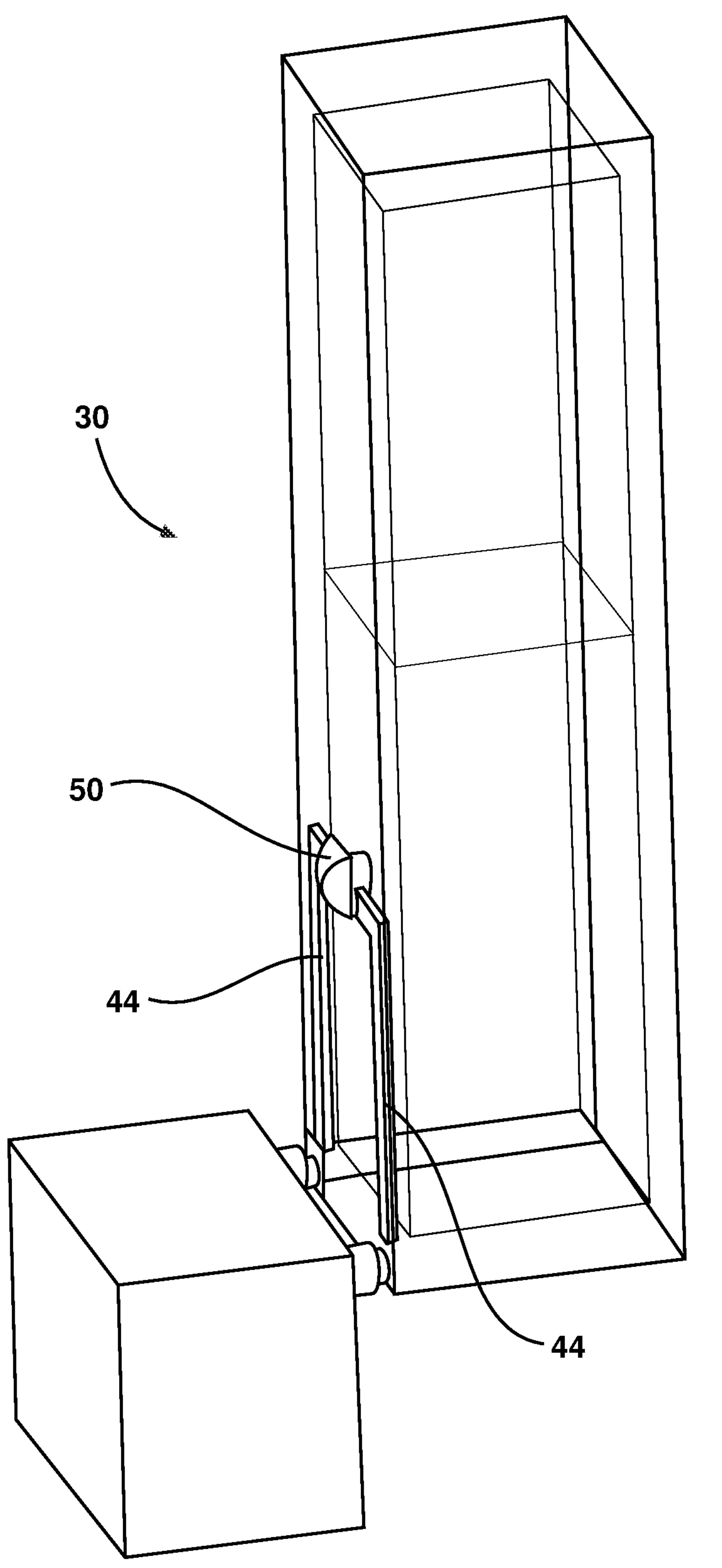
FIG. 5C is a scale perspective view of the cuvette of FIG. 5A.

Referring to FIGS. 5A-5C, additionally the cuvette 30 may have any of the aforementioned sensors 50 and/or camera 52 disposed on the wall thereof. The sensor 50 provides for real time monitoring of the temperature of the wall of the respective cuvette, vibration resulting from movement of animal life therein, the ISS 101 or transport vehicle 101, incident light, ambient pressure, etc. These data may be recorded on a data logger 43 for subsequent analysis. Prophetically a typical model computer available from Raspberry Pi of Cambridge, England is suitable for use as a data logger 43.

If desired, the indicia 33R may be disposed on a wall of the receptacle 11. This arrangement provides the benefit that the indicia 33R are permanent and may be used with cuvettes 30 having no indicia 33C thereon.

Figure 6A:
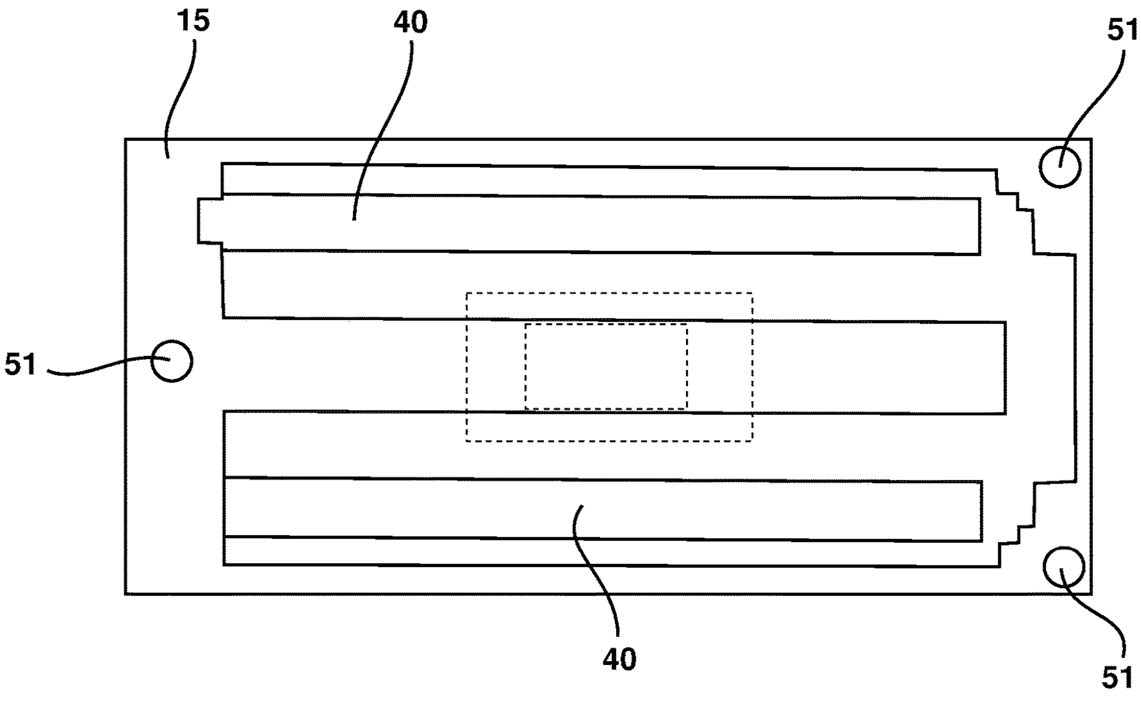
FIG. 6A is a scale bottom plan view of an alternative embodiment of a lid usable with the chamber of the present invention.
Figure 6B:
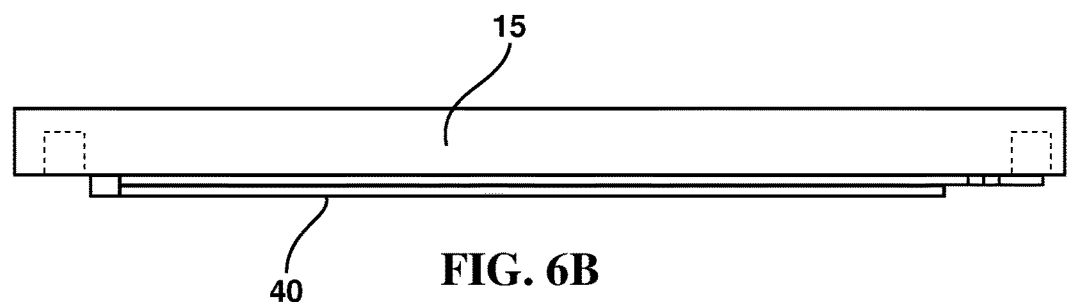
FIG. 6B is a side elevational view of the lid of FIG. 6A.

Referring to FIGS. 6A-6B, in an alternative embodiment, the lid 15 may further comprise LEDs, circuitry and/or the aforementioned magnets 51, sensors 50, camera 52, etc. disposed directly thereon. A generally flat LED profile provides the benefit of conserving space to meet the aforementioned volume specifications and providing more space for cuvettes 30 and other experimental components. Conductive images may be formed on the lid 15, side panel, partition 17, base 13 and/or cuvettes 30 according to the teachings of U.S. Pat. No. 8,784,593 to Wismann, the disclosure of which is incorporated herein by reference.

Figure 7A:
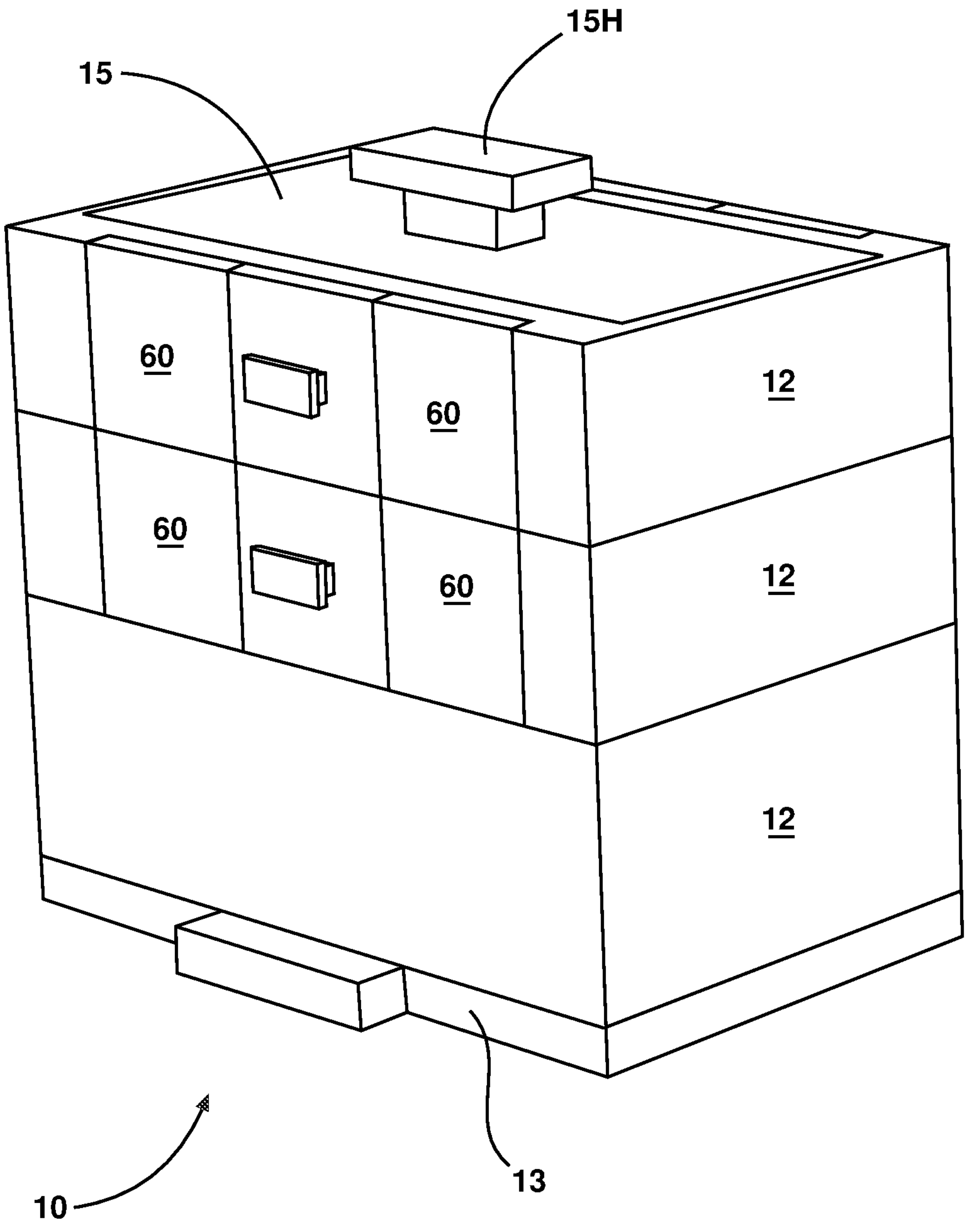
FIG. 7A is a scale perspective view of an alternative embodiment of a chamber according to the present invention.
Figure 7B:
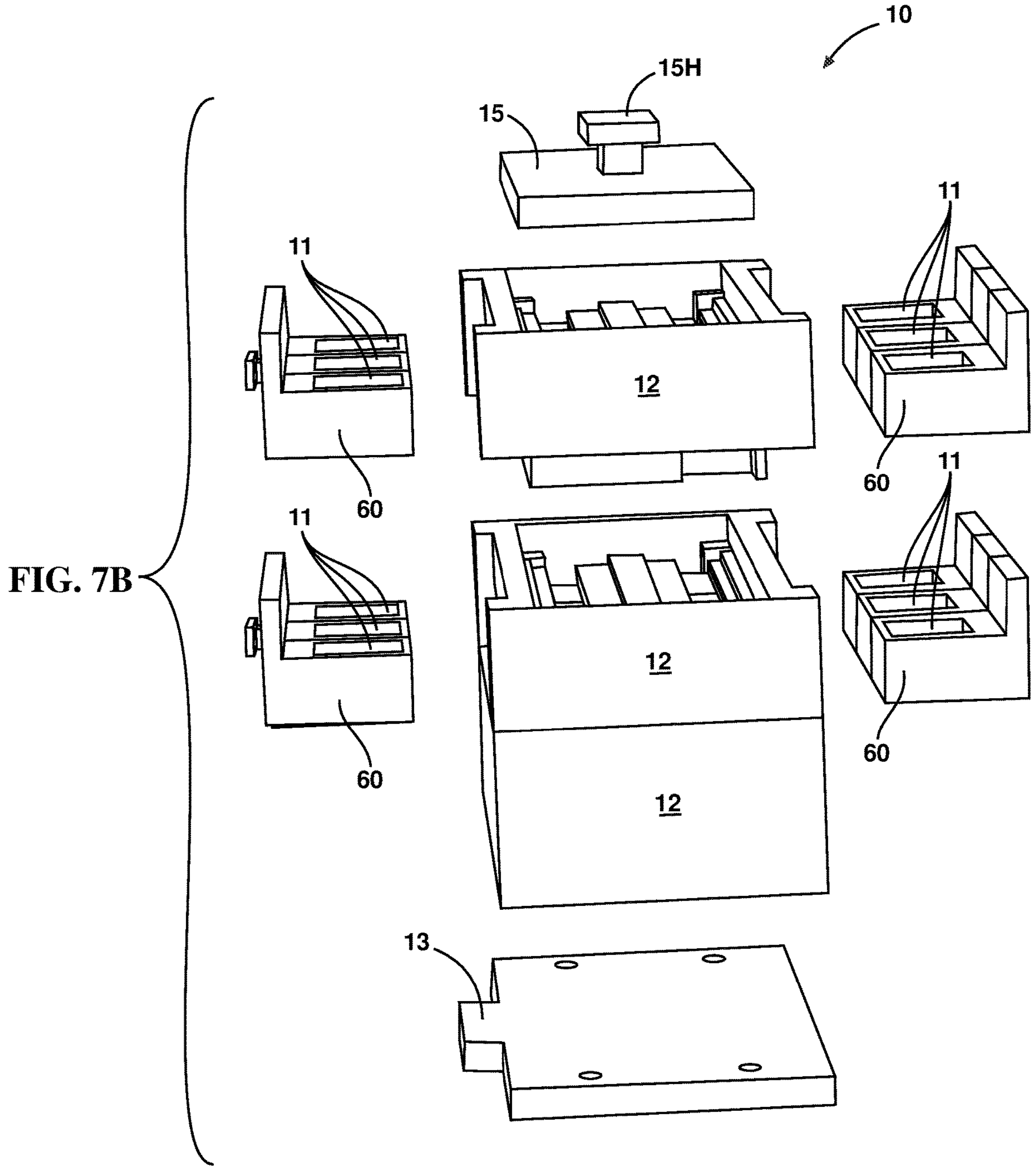
FIG. 7B is a scale exploded perspective view of the chamber of FIG. 7A.

Referring to FIGS. 7A-7B, in an alternative embodiment, the chamber 10 may have one or more drawers 60. Each drawer 60 accommodates a receptacle, and preferably a plurality of receptacles 11 therein. One or more cuvettes 30 may be disposed in each receptacle, as described above. This arrangement provides the benefit that cuvettes 30 can be removed from the chamber 10, and yet be protected by the drawer 60. The cuvettes 30 may be removed from the receptacles 11 in the drawer 60 or the living organisms 56 may be examined while the cuvette 30 in the drawer 60.

One of skill will understand that either embodiment of chamber 10, having the open front receptacles 11 or having the receptacles 11 in the drawers 60 may have any number of rows 19, drawers 60 and receptacles 11 therein or have individual receptacles 11. The chamber 10 may have rows 19 longer and/or shorter than shown in both embodiments. Likewise, the first embodiment may have stacked rows 19 of receptacles 11, similar to the stacked drawers 60 in the second embodiment. Either embodiment may have a modular construction, as shown, to increase the number of available simultaneous experiments. And one of skill will understand that a single space mission may have plural chambers 10, each chamber 10 having its own complement of cuvettes 30.

Referring back to FIG. 1B and FIG. 3, the growth medium 55 may comprise guar gum, a water-soluble natural polymer made from legumes called guar beans, algae, Java moss, natural sponge, biofilm, cellulose, etc. The growth medium 55 may include a magnetic sheet made according to US 2017/0196172 to Ejiri, the disclosure of which is incorporated herein by reference. The cuvette 30 may have a single growth medium 55 or plural growth media 55 therein, as desired for the particular experiment under consideration.

The growth medium 55 may be disposed near the midpoint of the cuvette, between the proximal end and distal end of the cuvette. This arrangement provides for growth of the living organisms 56, particularly plants, in space. On earth starch granules in embryonic root cells fall in the direction of gravity, orienting the plant growth. But in space there is no gravity influence, allowing the plants to grow bilaterally longitudinally within the cuvette 30 with the stems 56S and roots 56R growing in opposite directions from the growth medium 55. Alternatively, the growth media 55 may be disposed substantially throughout the cuvette 30.

The living organisms 56 may include fungi, animals and/or plants. Animals may include both prokaryotic organisms, including bacteria and archaea, and/or eukaryotic organisms. Plants may include both wild type plants and transgenic plants. Illustrative and nonlimiting fungi include *Trichoderma harzianum* fungus. Illustrative and nonlimiting animals include sea monkeys, brine shrimp and freshwater shrimp. Illustrative and nonlimiting plants include *Arabidopsis thaliana.*

All values disclosed herein are not strictly limited to the exact numerical values recited. Unless otherwise specified, each such dimension is intended to mean both the recited value and a functionally equivalent range surrounding that value. For example, a dimension disclosed as "40 mm" is intended to mean "about 40 mm." Every document cited herein, including any cross referenced or related patent or application, is hereby incorporated herein by reference in its entirety unless expressly excluded or otherwise limited. The citation of any document or commercially available component is not an admission that such document or component is prior art with respect to any invention disclosed or claimed herein or that alone, or in any combination with any other document or component, teaches, suggests or discloses any such invention. Further, to the extent that any meaning or definition of a term in this document conflicts with any meaning or definition of the same term in a document incorporated by reference, the meaning or definition assigned to that term in this document shall govern. All limits shown herein as defining a range may be used with any other limit defining a range of that same parameter. That is the upper limit of one range may be used with the lower limit of another range for the same parameter, and vice versa. As used herein, when two components are joined or connected the components may be interchangeably contiguously joined together or connected with an intervening element therebetween. A component joined to the distal end of another component may be juxtaposed with or joined at the distal end thereof. While particular embodiments of the present invention have been illustrated and described, it would be obvious to those skilled in the art that various other changes and modifications can be made without departing from the spirit and scope of the invention and that various embodiments described herein may be used in any combination or combinations. It is therefore intended the appended claims cover all such changes and modifications that are within the scope of this invention.

What is claimed is:

1. A method of testing living organisms in space, the method comprising the steps of:

on earth providing a chamber having a volume of less than or equal to 1.5 liters and being adapted for removably receiving a plurality of elongate cuvettes therein, the chamber having a base and an illumination lid remote therefrom, a first row of a first plurality of receptacles between the base and lid, and a second row of a corresponding second plurality of receptacles between the base and lid, each receptacle being sized to removably receive at least one respective cuvette therein, each cuvette having a proximal end and a translucent distal end longitudinally opposed thereto and juxtaposed with the illumination lid;

on earth disposing at least one living organism in each cuvette of a first plurality of cuvettes, to be in contacting with a growth medium disposed therein and maintaining the cuvettes at atmospheric pressure therein; on earth disposing the first plurality of cuvettes with the living organisms therein in the receptacles of the chamber to thereby impart artificial light from the illumination lid to the living organisms while in the first plurality of cuvettes;

transporting the chamber to the international space station for removal from earth gravity for an extended period; and returning the chamber with the first plurality of cuvettes having the living organisms therein to earth for analysis of the living organisms.

2. A method according to claim 1 further comprising the step of measuring growth characteristics of the living organisms aboard the international space station.

3. A method according to claim 1 further comprising the step of, during transport to the international space station, exposing the chamber to a vacuum of space without depressurizing the first plurality of cuvettes.

4. A method according to claim 3 wherein the step of exposing the chamber to the vacuum of space without depressurizing the first plurality of cuvettes comprises the step of performing an extra vehicular activity.

5. A method according to claim 1 further comprising the steps of:

providing a magnetic field to magnetically influence a first subset of the first plurality of cuvettes with living organisms therein and not influence a second subset of the first plurality of cuvettes having control living organisms therein; and comparing the effects of the magnetic field on first subset of living organisms to the second subset of control living organisms.

6. A method according to claim 5 wherein the step of influencing the first subset of cuvettes with a magnetic field comprises the step of juxtaposing a respective magnet with the proximal end of each cuvette of the first subset of cuvettes.

7. A method according to claim 6 wherein the step of not magnetically influencing the second subset of cuvettes comprises removably inserting a metal partition intermediate the respective magnets and the second subset of cuvettes.

8. A method according to claim 7 further comprising the steps of returning at least one cuvette with a living organism therein to earth for analysis of the living organism on earth.

* * * * *